United States Patent [19]
Nelson et al.

[11] Patent Number: 4,925,802
[45] Date of Patent: May 15, 1990

[54] METHOD FOR STIMULATING BIODEGRADATION OF HALOGENATED ALIPHATIC HYDROCARBONS

[75] Inventors: Michael J. K. Nelson, Redmond; Al W. Bourquin, Seattle, both of Wash.

[73] Assignee: Ecova Corporation, Redmond, Wash.

[21] Appl. No.: 288,614

[22] Filed: Dec. 21, 1988

[51] Int. Cl.$^5$ .................. D06M 16/00; C02F 3/00
[52] U.S. Cl. ................... 435/262; 210/610; 210/611; 435/264
[58] Field of Search ............ 435/262, 264; 210/610, 210/611

[56] References Cited

U.S. PATENT DOCUMENTS 3,979,283  9/1976  Prudom .
3,980,557  9/1976  Yall et al. .
4,452,894  6/1984  Olsen et al. .
4,477,570  10/1984  Coloruotolo et al. .
4,664,805  5/1987  Focht .
4,713,343  12/1987  Wilson, Jr. et al. .

OTHER PUBLICATIONS

Nelson, Michael J. K. et al., "Biodegradation of Trichloroethylene and Involvement of an Aromatic Biodegradative Pathway", *Applied and Environmental Microbiology*, vol. 53, No. 5, pp. 949–954, May 1987.
Nelson, Michael J. K. et al., "Aerobic Metabolism of Trichloroethylene by a Bacterial Isolate", *Applied and Environmental Microbiology*, vol. 52, No.2, pp. 383–384, Aug. 1986.

*Primary Examiner*—Sam Rosen
*Attorney, Agent, or Firm*—Christensen, O'Connor Johnson & Kindness

[57]  ABSTRACT

A method of biodegrading halogenated alipahtic hydrocarbons is disclosed comprising incubating the hydrocarbons with microorganisms capable of degrading halogenated aliphatic hydrocarbons together with a nontoxic, nongaseous substance that induces the biodegrading activity of said microorganisms. An example of the nontoxic, nongaseous substance is an aromatic amino acid, e.g. tryptophan.

13 Claims, No Drawings

METHOD FOR STIMULATING BIODEGRADATION OF HALOGENATED ALIPHATIC HYDROCARBONS

FIELD OF THE INVENTION

The present invention relates, in general, to an improved method for biodegradation of halogenated aliphatic hydrocarbons and, in particular, to the in situ biodegration of volatile chlorinated aliphatic compounds (VCA), e.g., trichloroethylene (TCE).

BACKGROUND OF THE INVENTION

The halogenated aliphatic hydrocarbon trichloroethylene (TCE) is a volatile, chlorinated compound of increasing concern as a ground water contaminant. TCE is potentially carcinogenic and is resistant to biological or abiological decomposition in subsurface waters. Conventional water treatment processes have been found to be ineffective in removing TCE from ground water. Results obtained with air stripping and adsorption to granular activated charcoal or Ambersorb resin, are more effective. These methods are present state-of-the-art technologies for remediation of VCAs. Although effective, they suffer from the fact that they simply transfer the contamination to another medium; either to the atmosphere (air stripping) or to solid medium (adsorption) which must then to disposed of as hazardous waste. The present invention results in conversion of the toxic compounds to nontoxic products.

The TCE degradation potential of microbes found in ground water systems has been examined. Evidence of anaerobic biodegration has been reported. Several studies suggest that TCE may be degraded under methanogenic conditions. However, the products of degradation include equally harmful metabolites, such as dichloroethylenes and vinyl chloride. Complete mineralization of TCE was obtained when nonsterile soils were exposed to natural gas in air, suggesting that methanotrophic microorganisms are capable of degrading TCE. A possible mechanism for the degradation of TCE by methanotrophs involves epoxidation of TCE by methane monooxygenase followed by nonbiological rearrangements that result in the formation of dichloroacetic acid, formate, and carbon monoxide, each of which would then be further degraded.

However, pure cultures of microoogranisms that degrades TCE has been reported in the literature, Nelson, M.J., et al., Applied Environ. Microbiol., 53:949–954(1987) and Nelson, M.J., et al., Applied Environ. Microbiol., 54:604–606 (1988), and are the subject of copending U.S. Patent Appl. No. 44,213, the disclosures of which is hereby incorporated by reference.

These pure cultures are used in a biodegradation method that includes incubating microorganisms capable of degrading halogenated aliphatic hydrocarbons by an aromatic degradative pathway, together with halogenated aliphatic hydrocarbons under conditions such that the aromatic degradative pathway is active. The method results in the conversion of the halogenated aliphatic hydrocarbons into nontoxic products, including carbon dioxide and inorganic chloride. The method is useful in decontaminating halogenated aliphatic hydrocarbon-polluted environments. Decontaminating systems can utilize such pure cultures in bioreactor-type systems. Alternatively, natural microbial communities or introduced microorganisms can be stimulated to degrade halogenated aliphatic hydrocarbons by addition to the contaminated site of an amount of an inducer sufficient to induce an aromatic degradative pathway by which the halogenated aliphatic hydrocarbons are degraded. Unfortunately, the requirement that an inducer, e.g., methane gas or aromatic compounds, be added to activate the degradative pathway limits the bioremediation utility of these newly discovered pure cultures. Before applicant's discovery, only two types of inducers were available for biodegradation methods. Aromatic compounds, e.g., phenol, are effective inducers but their in situ use is limited by the fact they are also undesirable environmental pollutants. An alterative approach utilizes methane gas an an in situ inducer. Although effective as an inducer for the degradation of certain contaminants, the gaseous nature of methane makes it more difficult to add in situ and, also, makes controlling the biodegradation process difficult.

Accordingly, it is an object of the present invention to provide a method for biodegradation of halogenated aliphatic hydrocarbons wherein a nontoxic, nongaseous compound is utilized as an inducer to the bacterial populations or organisms. It is an additional object of the present invention to provide a method for in situ biodegradation of halogenated aliphatic hydrocarbons wherein a nontoxic, nongaseous compound is utilized as an inducer.

Further objects and advantages of the present invention will be apparent from the discussion that follows.

SUMMARY OF THE INVENTION

The present invention is based on the discovery of innocuous, nontoxic, nongaseous inducers that stimulate microorganisms to degrade halogenated aliphatic hydrocarbons by incuding oxygenase-controlled pathways. Examples of such inducers include aromatic amino acids, such as tryptophan and C10–C20 linear alkanes. A significant advantage of an aromatic amino acid inducer is that they are natural, nontoxic substances, many of which are required nutrients for humans, and thus should be acceptable to regulator agencies, such as the U.S. Environmental Protection Agency, for in situ addition. These inducers are used in accordance with the present invention to stimulate the biodegradation of halogenated aliphatic hydrocarbons.

Accordingly, the present invention in its broadest aspect is directed to a method of biodegrading halogenated aliphatic hydrocarbons including incubating the halogenated hydrocarbons with microorganisms capable of degrading the halogenated hydrocarbons together with a nontoxic, nongaseous inducer that stimulates the biodegrading activity of the microorganisms. In a preferred embodiment, the incubating step occurs substantially in situ.

The halogenated aliphatic hydrocarbon can be a volatile chlorinated aliphatic (VCA) hydrocarbon, for example, a chlorinated ethylene. Applicant's method is particularly well suited for the biodegradation of trichloroethylene (TCE). The method typically employs microorganisms that are capable of degrading the halogenated aliphatic hydrocarbon by an aromatic degradative pathway.

DESCRIPTION OF THE PREFERRED EMBODIMENTS

Although the advantages of the inducers used in the present invention are more completely realized when the incubation occurs substantially in situ, the biodegrading method can be employed in a surface bioreactor. It is preferred for simplicity that the inducer and the target contaminant be concurrently incubated with the selected microorganisms. Alternatively, it may be advantageously for the method of the present invention to include the preliminary step of stimulating the selected microorganmisms with the inducer. Such stimulated microorganisms may then be added to the site of the contamination, with or without additional inducer.

Halogenated aliphatic hydrocarbons subject to degradation include, but are not limited to, volatile chlorinated aliphatic (VCA) hydrocarbons. VCAs include chloroethanes and chloroethylenes, for example, trichloroethylene (TCE), 1,1-dichloroethylene, cis-1,2-dichloroethylene, and choroethylene (vinyl chloride).

There are two types of microorganisms used in the present invention. Exogenous microorganisms introduced to the site can be specifically selected, mutated, genetically engineered to degrade particular halogenated aliphatic hydrocarbons by an aromatic degradative pathway. Alternatively, indigenous microorganisms, e.g., the natural halogenated aliphatic hydrocarbons by in situ addition of nontoxic, nongaseous inducers.

Microorganisms capable of degrading target halogenated aliphatic hydrocarbons can be selected from mixed cultures by growing the culture in the presence of an inducer capable of stimulating biodegradation, under conditions such that the culture is enriched for microorganisms capable of degrading the target hydrocarbon. Pure cultures of such microorganisms can then be isolated by subculturing the enriched population using techniques well known to one of skill in the art.

More specifically, microorganisms can be isolated as follows. Soil samples are taken from the natural flora. A target halogenated aliphatic hydrocarbon, in the presence or absence of an inducer, is added to each sample. Although the present invention is directed to the use of nontoxic, nongaseous inducers, e.g., tryptophan, in biodegradation, microorganisms useful in the present invention may be isolated using other types of inducers, e.g., phneol, and tested for stimulation by nontoxic inducers. Each sample is then analyzed for hydrocarbon degradation compared to sterile controls. For each sample showing significant target hydrocarbon degradation, aliquots of the sample are plated onto agar plates. Colonies of the microorganisms are grown and each is tested for its ability to degrade the target aliphatic hydrocarbons in the presence or absence of an inducer. example, strain G4 (a strain of *Pseudomonas cepacia* deposited at the American Type Culture Collection, Rockville, MD, on April 30, 1987, ATCC 53617) was isolated and used as follows. A water sample from a jolding pond at an industrail waste treatment facility for the Naval Air Station (NAS) in Pensacola, Fla., having a history of contamination with organochlorine compounds, was screened for possible TCE degradation. The sample was supplemented with concentrated stock solutions to yield a basal salts medium (R.Y Stainer, et. al., J. Gen. Microbiol., 43:159-271 (1966)), and 5-ml aliquots were dispensed into 30-ml screwcap culture tubes (18 by 150 mm). Tubes were sealed with Teflon-faced neoprene rubber septa secured by hole caps to allow access by syringe; TCE (50 nmol) was added as an aqueous stock by syringe through the septum of each tube. Samples (20 $\mu$l) of the headspace from each tube were analyzed periodically by gas chromatography for changes in TCE concentration. The injector, oven, and detector temperatures on the gas chromatography were 100°, 60° and 325° C., respectively. The carrier gas was H2 (1 ml/min) and the makeup gas was 90% argon-10% methane (45 ml/min through the detector).

The water sample was a substantial decrease in TCE concentration as compared to autoclaved controls. Subcultures of this sample metabolized TCE when filter-sterilized or autoclaved water from the original sampling site ("NAS water") was used to make up the basal salts medium for the experiments. Something in the NAS water samples apparently acts as an inducer to stimulate the biodegradation of the TCE. NAS water was therefore used in the medium for all subsequent tests for TCE metabolism. Aliquots of the water sample were plated on glucose medium (10 mM glucose, 0.05% yeast extract in basal salts medium) for isolation of colonies. Resulting isolates were grown in glucose medium to stationary phase, and 1 ml portions were added to 50 ml Wheaton serum vials containing NAS medium (10 ml of basal salts solution made up in NAS water and supplemented with 0.05% yeast extract). The vials were sealed with Teflon-faced neoprene serum stoppers and crimp caps, and TCE (50 nmol) was added as an aqueous stock by syringe through the septa. Changes in TCE concentrations in the medium after equilibration with the headspace of the vials were determined by extracting 1.5 ml samples with an equal volume of n-pentane and injecting 1.5 $\mu$l of the extract into the gas chromatograph under the conditions described above. Alternatively, all TCE extracted from the test bottles by whole bottle extraction. This method utilized addition of pentane to the bottles by syringe in an amount equivalent to the total aqueous volume of the sample (usually 10 ml), followed by thorough mixing. A 1.5 ml subsample of pentane phase was then removed by syringe and analyzed by GC. This method determines the total amount of TCE present in both aqueous an gas phase, and is repoted as TCE in aqueous phase ($\mu$g/ml). All subsequent experiments also followed this method for monitoring TCE metabolism. In this manner, a pure culture, designated strain G4, which degraded TCE was obtained.

Strain G4 is a nonmotile, gram-negative, rod-shaped bacterium which grows predominantly in pairs and short chains in logarithmic phase. The microbe was identified by the API ® Rapid NFT ® test as a strain of *Pseudomonas cepacia* (Table 1). Although strain G4 grows on a variety of substrates, including glucose, lactate, succinate, acetate, and ethanol, no growth is observed with methane (up to 50% of the culture headspace) or methanol.

Additional strains capable of degrading halogenated aliphatic hydrocarbons by an aromatic degradative pathway can be isolated from the natural flora using techniques comparable to that used to isolate G4 exctp that, instead of NAS water, one of the below-described inducers can be added to the medium to stimulate biodegradation.

The nontoxic, nongaseous inducers of the present invention that stimulate the metabolic pathways by which halogenated aliphatic hydrocarbons are biodegraded include substances capable of inducing oxygenases which exhibit broad enzyme specifically and are fortuitously capable of degrading volatile halogenated aliphatic hydrocarbons. The aromatic amino acid, such as phenylalanine, tyrosine, and tryptophan, are examples of such inducers. Also, linear alkanes of at least C10, preferably C10–C20, are nontoxic, nongaseous substances capable of inducing oxygenases.

TABLE 1

Identification of Strain G4 by API ® Rapid NFT ® Test

| | NO3 NO2 N2 | TRP | GLU | ADH | URE | ESC | GEL | PNPG | GLU | ARA | MNE |
|---|---|---|---|---|---|---|---|---|---|---|---|
| 24 h | + | − | − | − | − | − | − | + | + | | |
| 48 h | | | | | | | | | + | + | + |

| | MAW | NAG | MAL | GNT | CAP | ADI | MLT | CIT | PAC | OXI |
|---|---|---|---|---|---|---|---|---|---|---|
| 24 h | | | | | | | | | + | + |
| 48 h | + | + | − | + | + | − | + | +/− | + | + |

Gram: negative
Morphology: Rod
Motility: Nonmotile
Identification: *Pseudomonas cepacia*

Other suitable organisms could be selected by screening environmental samples, in a manner previously described for G4, by enriching with organic compounds known to require monooxygenases or dioxygenases for their degradation. Said enrichments could then be tested for the ability to degrade halogenated aliphatic hydrocarbons in a manner similar to that described for screening for TCE degraders which resulted in the discovery of strain G4. Alternatively, pure cultures of organisms known to degrade other organic compounds using oxygenases may be tested for halogenated aliphatic hydrocarbon degradation.

The invention is illustrated by way of the following nonlimiting exmaples:

EXPERIMENTAL CONDITIONS AND EXAMPLES

Culture conditions.

All media contained basal salts (MSB [*J. Gen. Micriobiol.* 43:159–271 (1966)]), and cultures were grown at 30° C. with shaking (200 rpm). Cultures were maintained on 10 mM glucose or 10 mM succinate.

Induced cultures of strain G4 were grown from a 5% inoculum on 20 mM sodium lactate-plus inducer as indicated for 20 hours. One ml (ca. $10^9$ cells) was used as inoculum for the experiments.

TCE degradation experiments.

TCE degradation experiments were similar to those described by Nelson et al. (*Appl. Environ. Microbiol.,* 52:383–384 (1986)) and used 50 ml serum bottles sealed with butyl rubber stoppers and crimp caps. Each bottle contained 10 ml of MSB, TCE, and inoculum as described below. Unless otherwise indicated, experiments were terminated after 24 hours of incubation at 26° C. TCE degradation was monitored by measuring TCE concentrations in the aqueous phase of the test bottles by pentane extraction and gas chromatography (see Nelson et al. (1986) cited above). TCE in solution does not equal total TCE in experiments because of its partitioning between the liquid and gas phases of the test bottles. However, dissolved TCE is proportional to total TCE added and thus serves as a reliable method of monitoring. No TCE remained in the gas phase when it was below detection limits in the aqueous phase.

Chloride analysis.

Chloride was determined with a model 94-17B chloride-specific electrode and a model 90-02 reference electrode calibrated with KCl standards made up in 0.1 M potassium phosphate buffer (pH 7.0) (P7 buffer). Alternatively, chloride ion concentration was determined spectrophotometrically (*Chem. Soc. Japan,* 29:860–864 (1956)). Experiments to detect the production of chloride were performed like TCE degradation experiments and contained 200 nmol of TCE and 1 mM phenol. P7 buffer replaced MSB, and phenol-induced, resuspended cultures of strain G4 were used as the inoculum. Results were corrected for background chloride. Time course experiments were performed by setting up replicate bottles and sacrificing bottles at various times.

EXAMPLE 1

Induction of TCE degradation by aromatic compounds

Two hundred nmol of TCE and 1 ml of a late-log-phase culture (ca. $3 \times 10^9$ CFU) of strain G4 grown on 20 mM lactate were used. Data are the means±standard deviations of triplicate experiments.

The data in Table 2 demonstrate that toluene, o-cresol, and m-cresol stimulated TCE degradation; m-xylene, sodium benzoate, and p-cresol did not stimulate TCE degradation. All of the above-listed compounds, with the exception of m-xyelen, were growth substrates for strain G4.

TABLE 2

| Compound added (1mM) | TCE remaining[a] (μM) |
|---|---|
| None | 3.35 ± 0.26 |
| Phenol | 0.04 ± 0.0 |
| Toluene | <0.02[b] |
| m-Xylene | 3.92 ± 0.08 |
| Sodium benzoate | 4.17 ± 0.29 |
| o- Cresol | <0.02 |
| m-Cresol | 0.07 ± 0.09 |
| p-Cresol | 4.04 ± 0.45 |

[a]After 24 h of incubation. A typical control with a sterile inoculum contained 3.5 μM TCE.
[b]Minimum detectable level.

EXAMPLE 2

Production of inorganic chloride by TCE degrading microorganism

When TCE was degraded by strain G4, stoiciometric amounts of inorganic chloride were produced. In two separate sets of experiments (three replicates each), 541±20 and 586±34 nmol of chloride were produced from 200 nmol of TCE, equal to 2.7 and 2.9 chloride ions per TCE molecule, respectively. Time course studies indicated that chloride was produced at a linear rate of 3.6 nmol/min (r=0.96), corresponding to the consumption of 1.2 nmol of TCE per min (assuming three chloride ions TCE molecule). Complete dechlorination occurred in 3 h; no further Cl- production was detectable after 5 h.

EXAMPLE 3

Transformation of other chloro-aliphatics by strain G4

Strain G4 was tested for the ability to transform a variety of chloroethylenes based on the release of chloride from the compounds (Table 3). 1,1-Dichloroethylene, cis-1,2-dichloroethylene and vinyl chloride appeared to be transformed with the release of about one Cl$^-$ per molecule.

TABLE 3

Test of Strain G4 for the Ability to Dechlorinate Chloroethylenes

| Compound | Chloride Produced[a] (nmol) | Chloride Per Molecule | Percentage Theoretical |
|---|---|---|---|
| 1,1-Dichloroethylene | 445 ± 93 | 1.5 | 74 |
| cis-1,2-Dichloroethylene | 344 ± 153 | 1.2 | 57 |
| Vinyl chloride | 505 ± 43[b] | 0.8 | 84 |
| trans-1,2-Dichloroethylene | 67 ± 51 | 0.2 | 11 |
| 1,1-Dichloroethane | −127 ± 34 | −0.4 | −21 |
| 1,2-Dichloroethane | 9 ± 128 | 0.2 | 1 |
| 1,1,1-Trichloroethane | −16 ± 138 | −0.1 | −3 |
| 1,1,2-Trichloroethane | −153 ± 26 | −0.8 | −26 |
| 1,1,2,2-Tetrachloroethane | 89 ± 26 | 0.6 | 15 |
| Tetrachloroethylene | −46 ± 105 | −0.3 | −8 |

[a]Background subtracted. Data are the means and standard deviations from three replicates. The compounds were added to yield 600 nmol of chloride-equivalents.
[b]Determined spectrophotometrically (Chem. Soc. Japan, 29:860–864 (1956)).

EXAMPLE 4

Other microorganisms tested for the ability to metabolize TCE

Several strains of bacteria capable of degrading various aromatic compounds were tested for the ability to metabolize TCE in the presence of their respective aromatic substrates (Table 4). Under the conditions tested, only two toluene-utilizers *P. putida* strain F1 (*Biochemistry*, 7:2653–2662 (1968)) and strian B5 (isolated using similar techniques) were capable of completely metabolizing TCE.

These two strains degraded toluene via 3-methylcatechol. Another toluene-utilizer, *P. putida* strain mt-2, did not metabolize TCE. This organism degrades toluene via oxidation of the methyl group to form benzoate and subsequent dioxygenation to form catechol. Two mutants of *P. putida* strain F1, defective in the toluene degradative pathway, were tested for the ability to metabolize TCE (Table 5). The mutant Pp106 lacking the first enzyme of the pathway, toluene-2,3-dioxygenase, did not show any substantial metabolism of TCE, although another mutant, Pp39D, lacing the next enzyme in the pathway, the dihydrodiol dehydrogenase, metabolized TCE as effectively as the parent strain.

TABLE 4

TCE Metabolism By Microorganisms That Degrade Aromatic Compounds[a]

| Organism | Aromatic Substrate | TCE Remaining (nmol) |
|---|---|---|
| *P. putida* NCIB 9816 | Naphthalene | 0.81 ± 0.06 |
| Beijerinkia sp. | Biphenyl | 0.66 ± 0.12 |
| *P. putida* strain mt-2 | Toluene | 0.75 ± 0.17 |
| *P. putida* strain B5 | Toluene | <0.02 |
| *P. putida* strain F1 | Toluene | <0.02 |
| None | None | 0.63 ± 0.02 |

[a]Cultures used for inoculum were grown overnight on 10 mM glucose medium and 1 ml of each was used as inoculum. The indicated aromatic substrates were included in the TCE metabolism experiments at 1 mM. At initiation of the experiments, 50 nmol TCE was added and samples were incubated for 24 hours.

TABLE 5

Metabolism of TCE by Mutants of *P. putida* F1 Unable to Degrade Toluene[a]

| Strain | Defective Enzyme | TCE remaining (nmol) |
|---|---|---|
| Parent strain | None | <0.02 |
| Pp 106 | Toluene dioxygenase | 2.98 ± 0.09 |
| Pp 39D | Dihydrodiol dehydrogenase | <0.02 |
| None | — | 3.84 ± 0.13 |

[a]Toluene at 1 mM replaced phenol in these TCE metabolism experiments.

EXAMPLE 5

Induction of Biodegration of TCE by Strain G4 with Tryptophan

A preferred embodiment of the present invention is the utilization of microorganisms stimulated by addition of tryptophan to degrade volatile halogenated aliphatic hydrocarbons. In particular, it was discovered that the addition of tryptophan to cultures of strain G4 stimulated the organism to degrade TCE (Table 6). Tryptophan was not as effective as phenol on a per molar basis, but was shown to effect up to an 84 percent removal of TCE in batch studies. Higher efficiencies may be obtained with higher concentrations of tryptophan or in continuous operation. It is anticipated that other naturally occurring microorganisms may also be stimulated to degrade TCE by exposure to tryptophan. In situ degradation may thus only require addition of tryptophan. Alternatively, strain G4 or similar isolates may be added to the site or used in a bioreactor in conjucntion with tryptophan.

TABLE 6

Degradation of TCE by Strain G4 When Stimulated with Tryptophan

| Compound Added | TCE Remaining[1] | Percent No Addition |
|---|---|---|
| None | 1.08 ± 0.23 | 100.0 |
| Phenol 1 mM | 0.01 ± 0.002 | 1.0 |
| Tryptophan 1 mM | 0.66 ± 0.12 | 60.8 |
| Tryptophan 2 mM | 0.39 ± 0.04 | 36.3 |
| Tryptophan 4 mM | 0.17 ± 0.05 | 15.4 |

[1]Triplicate Experiments. Data are the mean ± standard deviations.

EXAMPLE 6

Degradation of TCE at Low Temperature By Strain G4 and NAtural Microflora

Degradation in situ will occur at lower temperatures than is normally optimal for microbial biodegradative activity. Strain G4 degraded TCE at temperatures expected in ground water aquifers when stimulated with tryptophan (Table 7). Natural microflora from a freshwater lake also degraded some TCE (15% of that added) at these temperatures when stimulated with tryptophan although much lower quantities were degraded than by strain G4.

TABLE 7

Degradation of TCE by Strain G4
and Natural Microflora at 15° C.

| Culture | Inducer | TCE (μg/ml) | Percent Remaining[1] |
|---|---|---|---|
| Natural Microflora[2] | Tryptophan | 1.92 ± 0.09 | 86 |
| Strain G4 | Tryptophan | 0.072 ± 0.03 | 3 |
| None | None | 2.19 ± 0.15 | 98 |

[1]After four days of incubation at 15° C. TCE determined by whole bottle extraction. TCE at initiation of experiment = 2.23 ± 0.12 μg/ml (100%).

[2]Natural microflora used were from a water sample obtained from Lake Sammamish, Redmond, Washington. The organisms were cultured by the addition of MSB and 2 mM phenol to 100 ml of lake water and incubation at 15° C. for three days followed by subculturing 4 ml of this enrichment for 5 days in 100 ml of MSB medium containing 2 mM DL-tryptophan.

EXAMPLE 7

Degradation of TCE in a Simulated Aquifer

A simulated sand aquifer was constructed in the laboratory in a covered glass box to determine the effectiveness of stimulating strain G4 to degrade TCE in situ and in the absence of aromatic inducers. The flow rate through the aquifer was maintained at a linear flow-rate of 90 cm per day resulting in complete turnover of the system every 12 hours. The volume flow-rate was 10 ml/min and the total liquid content of the unit was 8.1 liter. The water contained 1 to 3 ppm TCE contamination and was ammended with inorganic nutrients to support biological growth. TCE was monitored in samples from wells taken 10 cm upgradient and 20 cm downgradient of the point of introduction (referred to as "active zone") of the organisms and the inducer (tryptophan). At T=Zero $2 \times 10^{10}$ CFU of strain G4 grown overnight in 200 lm of 4mM tryptophan/MSB, was introduced through the recharge wells. A 10 mM stock solution of DL-tryptophan (Central Soya, Inc.) was started to the recharge wells at a rate of 2 ml/min. This should results in a final concentratio of 1.7 mM tryptophan after dilution in the aquifer. Monitoring TCE concentrations over 4 days indicated that a significant drop in TCE concentration had occurred. TCE concentrations downgradient of the active zone were 71–96 percent lower than the TCE concentration upgradient (Table 8).

TABLE 8

TCE Concentrations in a Simulated Aquifer Before and After Passage Through the Active Zone

| Sampling Time[1] | | TCE Concentration (ppm) | | |
|---|---|---|---|---|
| | | Up Gradient | Down Gradient | Percent Removal[2] |
| Before Inoculation | | 1.8 | 2.2 | −22 |
| At Inoculation | (+4 hours) | 0.6 | 0.75 | −20 |
| After Inoculation | (+48 hours) | 2.2 | 0.68 | 71 |
| | (+60 hours) | 3.2 | 0.14 | 96 |
| | (+72 hours) | 2.1 | 0.24 | 89 |
| | (+96 hours) | 2.7 | 0.11 | 96 |

[1]Relative to time of introduction of strain G4.
[2]Corrected for dilution with inducer solution.

The foregoing invention has been described in some detial by way of examples for purposes of clarity and understanding. Various combinations in form and detail can be amde without departing from the scope of the invention.

The embodiments of the invention in which an exclusive property or privilege is claimed are defined as follows:

1. A method of biodegrading halogenated aliphatic hydrocarbons comprising incubating said hydrocarbons with microorganisms capable of degrading said hydrocarbons by components of an oxygenase-controlled pathway, together with at leastone aromatic amino acid that stimulates said biodegrading activity of said microorganisms.

2. A method according to claim 1 wherein said incubating step occurs substantially in situ.

3. A method according to claim 1 wherein said halogenated aliphatic hydrocarbons are volatile chlorinated aliphatic (VCA) hydrocarbons.

4. A method according to claim 3 wherein said VCA hydrocarbons are chlorinated ethylenes.

5. A method according to claim 4 wherein said chlorinated ethylene is trichloroethylene (TCE).

6. A method according to claim 1 wherein said aromatic amino acid is tryptophan.

7. A method according to claim 1 wherein said microorganisms are aromatic hydrocarbon degrading bacteria.

8. A method according to claim 1 wherein said microorganisms are of the genus Pseudomonas.

9. A method according to claim 8 wherein said microorganisms are *Pseudomonas putida*.

10. A method according to claim 9 wherein said microorganisms are *Pseudomonas putida* F1.

11. A method according to claim 1 wherein said microorganisms are strain G4.

12. A method according to claim 1 wherein said miroogranisms are *Pseudomonas cepacia*.

13. A method according to claim 1, wherein said microorganisms are indigenous microorganisms.

* * * * *

UNITED STATES PATENT AND TRADEMARK OFFICE
CERTIFICATE OF CORRECTION

PATENT NO. : 4,925,802

DATED : May 15, 1990

INVENTOR(S) : Nelson et al.

It is certified that error appears in the above-identified patent and that said Letters Patent is hereby corrected as shown below:

| Title Page | Line | Error |
|---|---|---|
| Item [57] ABSTRACT | 2 | "alipahtic" is changed to --aliphatic-- |
| Column | | |
| 1 | 10 | "biodegration" is changed to --biodegradation-- |
| 1 | 28 | "to" is changed to --be-- |
| 1 | 33 | "biodegration" is changed to --biodegradation-- |
| 1 | 47 | "microogranisms" is changed to --microorganisms-- |
| 2 | 8 | "applicant's" is changed to --applicants'-- |
| 2 (first occurrence) | 13 | "an" is changed to --as-- |
| 2 | 34 | "incuding" is changed to --inducing-- |
| 2 | 41 | "regulator" is changed to --regulatory-- |
| 2 | 57 | "Applicant's" is changed to --Applicants'-- |
| 3 | 15 | "choroethylene" is changed to --chloroethylene-- |
| 3 | 22 | after "natural" --microbial flora at the site of contamination, can be stimulated to degrade-- has been inserted |
| 3 | 42 | "phneol" is changed to --phenol-- |
| 3 | 50 | after "inducer.", the following new paragraph has been inserted: --In a preferred embodiment, a pure microorganism culture can be used. For-- |

UNITED STATES PATENT AND TRADEMARK OFFICE
CERTIFICATE OF CORRECTION

PATENT NO. : 4,925,802

DATED : May 15, 1990

INVENTOR(S) : Nelson et al.

It is certified that error appears in the above-identified patent and that said Letters Patent is hereby corrected as shown below:

| Column | Line | Error |
|---|---|---|
| 3 | 54 | "jolding" is changed to --holding-- |
| 3 | 54 | "industrail" is changed to --industrial-- |
| 4 | 6 | "was" is changed to --caused-- |
| 4 | 38 | "an" is changed to --and-- |
| 4 | 39 | "repoted" is changed to --reported-- |
| 4 | 56 | "exctp" is changed to --except-- |
| 5 | 30 | "exmaples" is changed to --examples-- |
| 5 | 45 | "Micri-obiol." is changed to --Microbiol.-- |
| 6 | 37 | "m-xyelen" is changed to --m-xylene-- |
| 6 | 57 | "stoiciometric" is changed to --stoichiometric-- |
| 7 | 55 | "lacing" is changed to --lacking-- |
| 8 | 43 | "conjuention" is changed to --conjunction-- |
| 8 | 58 | "NAtural" is changed to --Natural-- |
| 9 | 40 | "organisms" is changed to --organism-- |
| 9 | 44 | "200 lm" is changed to --200 ml-- |
| 9 | 49 | "results" is changed to --result-- |
| 9 | 49 | "contratio" is changed to --concentration-- |

UNITED STATES PATENT AND TRADEMARK OFFICE
CERTIFICATE OF CORRECTION

PATENT NO. : 4,925,802

DATED : May 15, 1990

INVENTOR(S) : Nelson et al.

It is certified that error appears in the above-identified patent and that said Letters Patent is hereby corrected as shown below:

| Column | Line | Error |
|---|---|---|
| 10 | 17 | "detial" is changed to --detail-- |
| 10 | 19 | "amde" is changed to --made-- |
| 10 (Claim 1, line 5) | 28 | "leastone" is changed to --least one-- |
| 10 | 54 | "microogranisms" is changed to --microorganisms-- |

Signed and Sealed this

Seventeenth Day of September, 1991

Attest:

HARRY F. MANBECK, JR.

*Attesting Officer*    *Commissioner of Patents and Trademarks*